United States Patent [19]

Berdahl

[11] 4,053,774

[45] Oct. 11, 1977

[54] X-RAY EXPOSURE SENSOR AND CONTROLLER

[75] Inventor: C. Martin Berdahl, Sierra Madre, Calif.

[73] Assignee: California Institute of Technology, Pasadena, Calif.

[21] Appl. No.: 695,175

[22] Filed: June 11, 1976

Related U.S. Application Data

[63] Continuation-in-part of Ser. No. 603,109, Aug. 8, 1975, abandoned.

[51] Int. Cl.² ............................................. G01J 1/42
[52] U.S. Cl. .................................. 250/355; 250/367; 250/413
[58] Field of Search .............. 250/322, 354, 355, 401, 250/402, 361, 369, 413, 367

[56] References Cited

U.S. PATENT DOCUMENTS

| | | | |
|---|---|---|---|
| 2,488,315 | 11/1949 | Morgan et al. | 250/322 |
| 2,829,273 | 4/1958 | Fransen | 250/322 X |
| 2,837,657 | 6/1958 | Craig et al. | 250/322 |
| 3,792,267 | 2/1974 | Westerkowsky | 250/322 |

Primary Examiner—Davis L. Willis
Attorney, Agent, or Firm—Lindenberg, Freilich, Wasserman, Rosen & Fernandez

[57] ABSTRACT

An exposure controller for x-ray equipment is provided, which comprises a portable and accurate sensor which can be placed adjacent to and directly beneath the area of interest of an x-ray plate, and which measures the amount of exposure received by that area, and turns off the x-ray equipment when the exposure for the particular area of interest on the x-ray plate reaches the value which provides an optimal x-ray plate.

18 Claims, 5 Drawing Figures

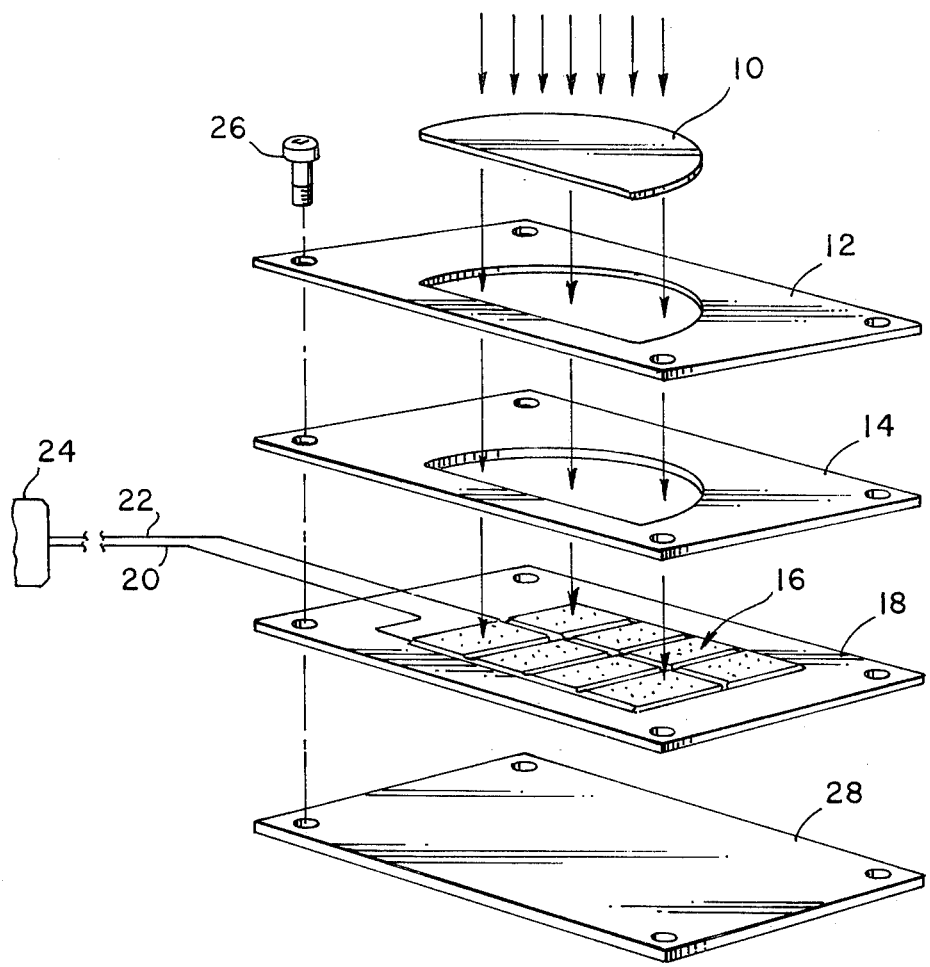
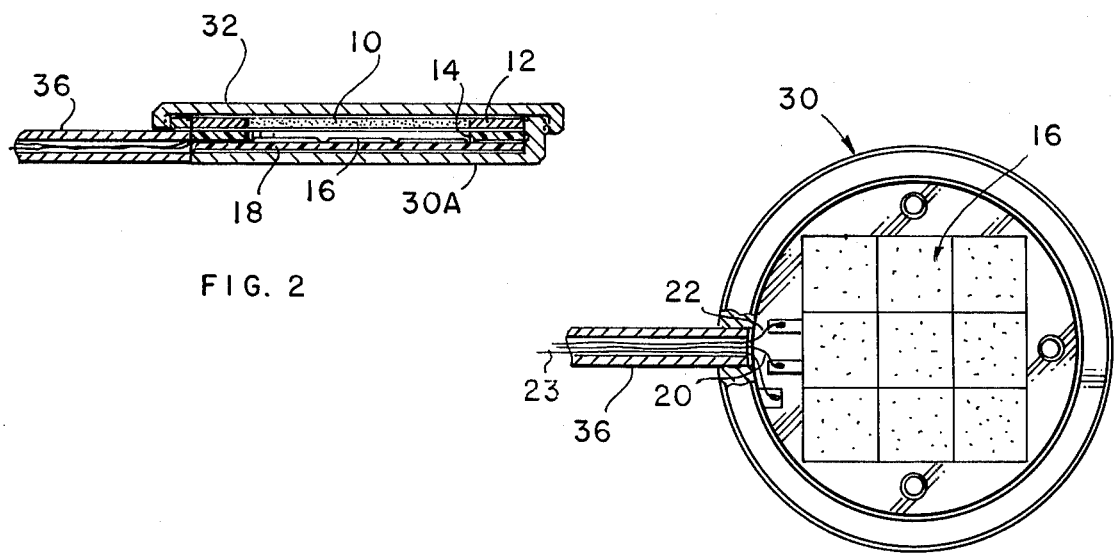
FIG. 1
FIG. 2
FIG. 3

X-RAY EXPOSURE SENSOR AND CONTROLLER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

CROSS REFERENCE TO RELATED APPLICATION

This application is a continuation-in-part application of application Ser. No. 603,109, filed Aug. 8, 1975 now abandoned.

BACKGROUND OF THE INVENTION

This invention relates to a portable x-ray exposure sensor for controlling the period of exposure of film to obtain the optimal result for the object being photographed.

Mammography is becoming more important in the detection of early carcinoma of the breast. In this regard, enhancing the quality of the mammographic image is a necessary prerequisite, if the largest number of early malignancies are to be detected. In order to enhance film quality, many factors must be controlled, one of the most important of which is film density or blackening. Despite extensive experience, operators have found it advisable to make a series of exposures of varying duration to obtain films suitable for diagnosis. Even with great care, it is sometimes necessary to recall the patient for further retakes. This occurs because of the anatomical differences between breasts, and in particular the ratio of fat to glandular and fibrocystic elements varies greatly between different breasts and this variation cannot be determined by physical examination.

The extra film exposures involve film and labor costs and the additional x-radiation imposed on the patient involves health hazards which would be desirable to avoid. An exposure controller which can provide a better accuracy of film exposure than the best operator estimates would produce savings in film costs, operator labor, and minimize the dangers that can result from excessive exposure of the patient to x-radiation.

One of the problems with previous types of x-ray exposure control devices, such as is shown in U.S. Pat. No. 2,488,315, is that they are fixed in location, complicated, not sufficiently sensitive for use with "soft" x-rays, such as are used for mammographs, and are not sufficiently effective for controlling exposure for the study of small areas.

OBJECT AND SUMMARY OF THE INVENTION

An object of this invention is the provision of a novel x-ray exposure control apparatus which is sufficiently sensitive for controlling exposure with "soft" x-rays.

Another object of this invention is the provision of a novel portable x-ray exposure control apparatus.

Still another object of this invention is the provision of an x-ray exposure control device suitable for controlling x-ray exposure in small areas of interest.

Yet another object of this invention is the provision of a novel and useful x-ray to electrical signal transducer.

The foregoing and other objects of this invention are achieved by x-ray controller apparatus which is positioned behind the x-ray film at the location of interest. The control apparatus itself comrises a sensor having a small size, comprising a housing wherein there is a scintillator which generates light when bombarded by x-rays, and solar cells, which generate an electrical voltage both in response to the x-rays as well as to the light from the scintillator, whereby the sensitivity of the apparatus to low-level x-ray, or soft x-ray, is achieved.

The novel features of the invention are set forth with particularity in the appended claims. The invention will best be understood from the following description when read in conjunction with the accompanying drawings.

BRIEF DESCRIPTION OF THE DRAWINGS

FIG. 1 is an exploded, isometric view of the invention.

FIGS. 2 and 3 are respectively views in elevation and plan illustrating the manner in which this invention is placed in a housing.

DESCRIPTION OF THE PREFERRED EMBODIMENTS

Figure 4:
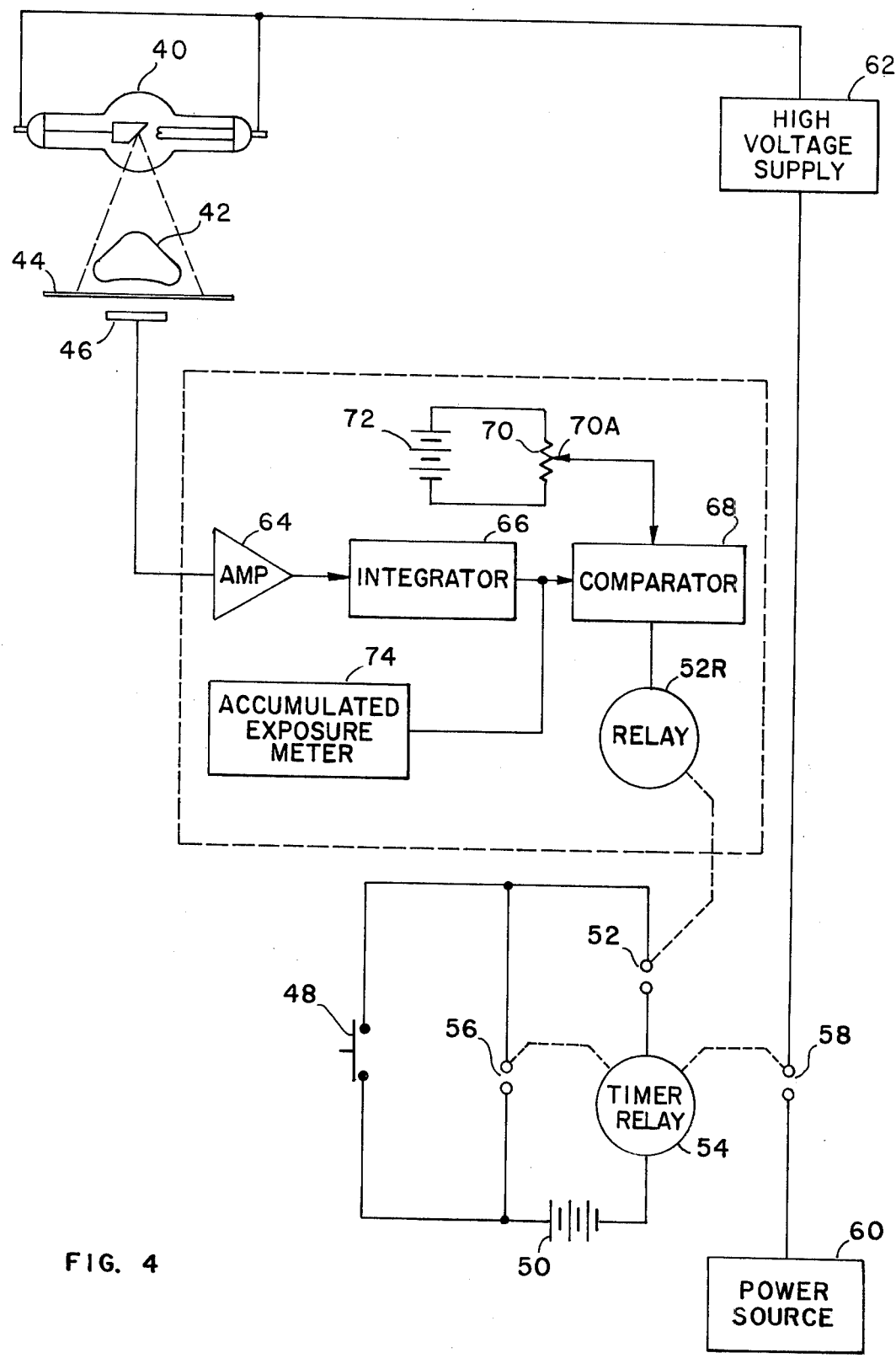
FIG. 4 is a schematic block diagram of a circuit arrangement with which this invention is used for controlling x-ray exposure.

Referring now to FIG. 1, there may be seen the components which when assembled constitutes an embodiment of this invention. These comprise a scintillator sheet 10, which, by way of example, is a sheet of material, such as Cronex, made by the DuPont Co., in Delaware, or "Min-R" screen, made by Eastman Kodak Co., Rochester, N.Y. which generates light or photons when impacted by x-rays. The x-rays also pass through the material. The scintillator sheet is supported in a lead mask 12, which blocks x-rays from passing through regions other than the desired area of the scintillator sheet.

An electrical insulator sheet 14, which is an identical image of the lead mask with respect to the open and closed areas is provided next, and is used to separate the conductive lead mask from a plurality of solar cells, such as 16. In the embodiment of the invention there is shown, by way of example, an array of eight solar cells, sometimes also called photovoltaic cells, which are individually supported on an insulator substrate 18. The open areas of the lead mask and the insulator allow both x-rays and photons to impinge on these solar cells. The voltages generated by the solar cells are added serially by means of interconnections, not shown, and are then applied to two leads, respectively 20, 22, which are brought out to a connector plug 24.

The insulator substrate together with the other components shown in the drawing, are all attached by suitable screws, such as 26, to a mounting plate 28.

Referring now to FIGS. 2 and 3, there may be seen views in elevation and plan which illustrate the container 30 as a cylindrical shape, this is by way of illustration, and not by way of limitation. The container is hollow and has the bottom 30A thereof, closed. Placed on the bottom of the container, which acts as the mounting 28 shown in FIG. 1, is the insulating substrate 18. This may be a printed circuit mounting board upon which the solar cells 16 are positioned. Over the solar cells, there is positioned the insulating board 14. The scintillator sheet is placed within the opening in the insulator board to be supported adjacent to the solar cells.

The lead mask 12 may be placed on top of the insulator board 14, or, preferably, may be placed near the top of the case. A suitable optic cover 32, of a material which is substantially transparent to x-rays may be used as the cover for closing the hollow space in the case. Three leads are taken from the case, two of these 20, 22 are from the series connected solar cells, and the third 23, is a ground lead. If desired, the case may be fitted with a handle, 36, of a suitable length so that the exposure sensor may be placed and held at the location where it is desired the optimum x-ray exposure for a film being taken, to occur. The handle length is determined by a length required for the safety of the person holding it, or preferably the length required so that the handle may be clamped in a suitable type of stand.

By way of illustration, and not to serve as a limitation, the diameter of the outside of the case 30 in an embodiment of the invention which was built, is on the order of 2 inches. The thickness of the case was on the order of ¼ inch. The area covered by the solar cells is on the order of 20 square centimeters.

FIG. 4 is a block schematic diagram of the electrical circuitry which is employed, by way of example, with the embodiment of the invention. An x-ray tube 40, when energized emits x-rays at the subject 42, behind which there is placed the photographic film 44. The sensor 46, in accordance with this invention is placed adjacent to and beneath the film at the location at which it is desired to obtain an optimum exposure.

When it is desired to initiate the operation of the system, a momentary switch 48, is moved to close a pair of contacts whereby current from a battery 50, may be applied through a pair of normally closed contacts 52, to a timer relay 54. The normally closed contacts 52 are controlled by a relay 52R. The timer relay 54 controls two sets of normally open contacts, respectively 56 and 58. The normally open contacts 56 will maintain power applied from the battery 50 to the timer relay 54 once the timer relay has been energized, whereby the normally open contacts 56 and 58 are held closed. Accordingly, after a momentary activation of the start exposure switch 48, timer relay 54 is held in an energized or an operating position through a circuit from the battery 50 through contacts 56 and 52.

A power source 60 supplies 110 volt ac through the, now-closed, contacts 58 to energize a high voltage supply 62, which applies the required energization voltage to the x-ray tube 40.

The output voltage of the sensor 46 is applied to an amplifier 64 whose output is applied to an integrator 66, to be integrated. The integrator circuit 66 is a well-known circuit which integrates the voltage applied to its input for as long as that voltage is applied. The output of the integrator 66 is applied to a comparator 68, which has as its other input a reference voltage. This reference voltage is derived from a potentiometer 70, which is connected across a reference potential source 72. The setting of the potentiometer arm 70A along the potentiometer slider, provides a reference voltage representative of an exposure, or dose, required for the integrator output to attain. When that occurs, the relay 52R is operated whereby the normally closed contacts 52 are opened interrupting the power supplied to the timer input relay. The timer relay 54 then becomes inactivated, opening the normally open contacts 56 and 58. This turns off the supply of power to the x-ray tube 40 and terminates the x-ray exposure.

Information as to optimum exposure dose for x-ray film is provided by the manufacturers of the film. The potentiometer can be calibrated in terms of these doses by measuring the voltage output of the integrator or the exposure levels indicated by the manufacturers. Then, the potentiometer slider 70A is moved until the voltage measured from the potentiometer equals the voltage derived from the integrator. These potentiometer settings for obtaining voltages equal to the integrator output voltages can then be marked in units or terms of exposure or dose. Thereafter exposure selection is achieved by the setting given to the potentiometer slider arm 70A.

If desired, this invention can also be used as an accumulated exposure indicator, or dosimeter. The output of the integrator can be calibrated in terms of the accumulated exposure from the x-ray tube. A voltmeter, indicated in the drawing as the accumulated exposure meter 74, can then be calibrated to indicate for each voltage reading what the accumulated x-ray exposure is whereby an operator may manually cut off x-ray exposure if desired.

The novel sensor can be used with x-ray equipment which produces radiation energy from an extremely low level of 10 Kev up to levels of 100 Kev or higher. It is applicable to all medical soft x-ray diagnosis equipment, such as found in clinics and hospitals. It can also be used for providing precisely measured doses of x-radiation for therapeutic purposes. While without the scintillator sheet, the solar cells will produce a given current flow in response to x-rays falling thereon, which is proportional to the instantaneous intensity of the x-rays received, by the use of the scintillator sheet, since solar cells are sensitive to both x-rays and to visible photons emitted from the scintillator, an increase in sensitivity is realized which exceeds the sensitivity of the solar cells alone by about 50% at low energy levels and considerably more at high energy levels. It is the high sensitivity of this sensor which makes possible its use in a controller for low energy mammographs for example. Because of the small size of the invention, it is obviously portable and may be used with portable x-ray equipment. The sensor can be used with almost any size x-ray film. Where an x-ray is being taken, it is placed adjacent to the back of the x-ray film at the region where the optimum exposure is desired in order to insure an optimum result for that particular region.

It has been found that, although the x-radiation to which the scintillator sheet and solar cells are exposed produces a current flow in the solar cell layer, these structures are substantially transparent to x-radiation. Thus, the impinging x-rays suffer only slight diminution in passage through the scintillator sheet and the silicon of the solar cells. Accordingly, in order to increase the output from the x-ray detector for a given quantity of radiation, one can stack layers of solar cell material and scintillator sheets one behind the other and thus the sensor will provide a substantially higher output for a constant radiation level, the output being nearly in proportion to the number of assemblies which are stacked, less the losses in each layer. For this purpose, the output of each layer of solar cells is connected in a series arrangement.

Figure 5:
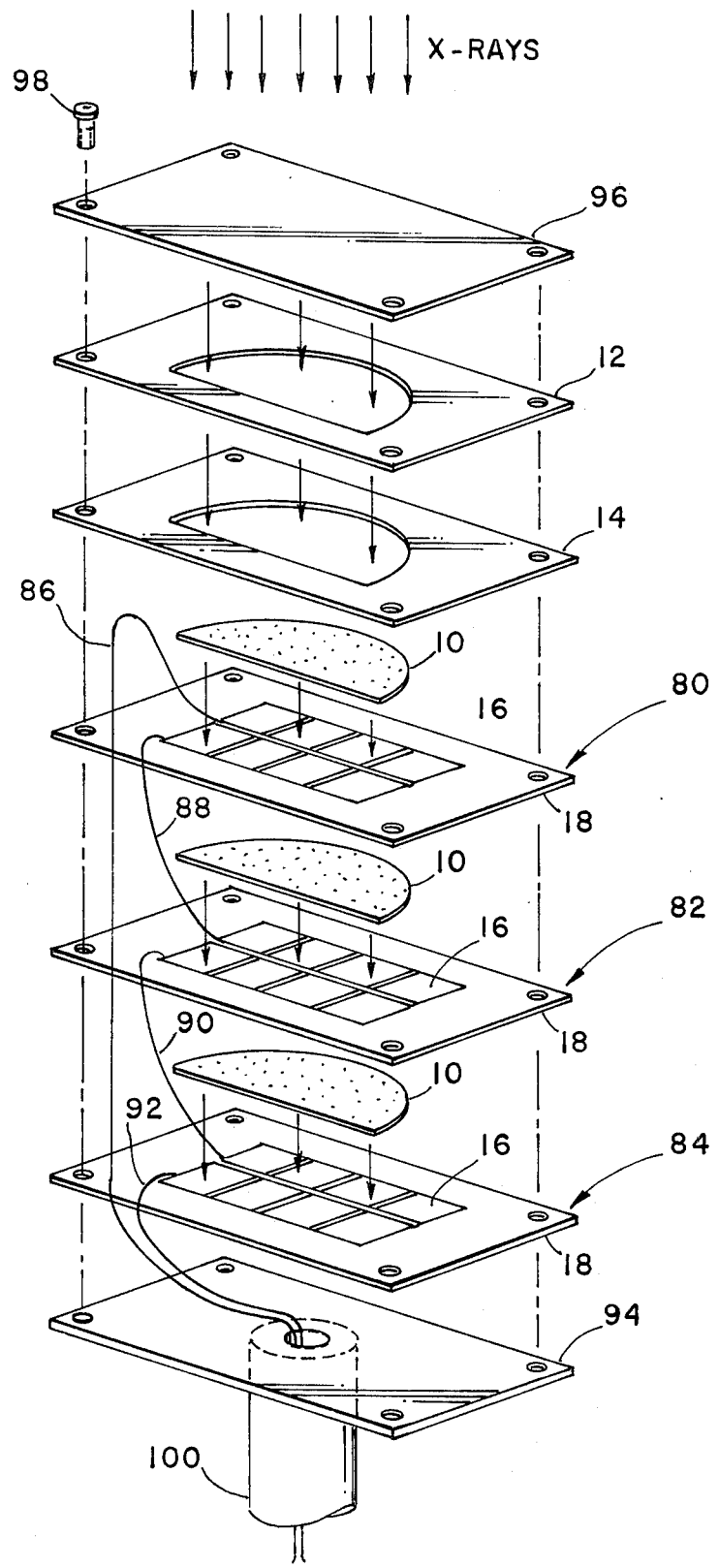
FIG. 5 is an exploded isometric view of an embodiment of the invention which permits an increase in its sensitivity.

FIG. 5 is an exploded view illustrating an embodiment of the invention whereby the sensitivity to x-ray exposure may be considerably increased. The reason for increasing the sensitivity to exposure arises because an x-ray film and scintillator combination has been made available recently, which is much faster than any previously available film by a factor of 15 to 1. In order to obtain appropriate exposure data for such a fast film, it is necessary and desirable to considerably increase the sensitivty of an x-ray exposure sensor. Similar functioning parts to those shown in FIG. 1 will be given the same reference numeral.

FIG. 5, shows, by way of example, three of the scintillator sheet-solar cell layers respectively 80, 82 and 84. One can use as many as are required to give a desired sensitivity, limited of course by the attrition caused to the x-rays in passing through a scintillator sheet-solar cell layer. These are packaged one adjacent to the other. Each layer has the same structure as was described for the layer in FIG. 1. The solar cells in each layer are connected in series, as was described in connection with FIG. 1. The output from each layer is connected in series by means of the wires 86, 88, 90, 92, which are led out of the package through a hole in a brass mounting plate 94. This brass mounting plate 94 is at the bottom of the stack of solar cells. At the top of the stack, there is a cover 96, which can be opaque to ambient light but is transparent to x-rays. This is followed by the lead mask 12 and the insulator 14, as shown in FIG. 1. The various layers 80, 82, 84 are fastened together by screws such as 98, passing through holes in the four corners of the respective sheets in the stacks. A handle 100 may be attached to the brass mount 94. The output leads may be connected to a control arrangement such as shown in FIG. 4. It should be appreciated that this arrangement of the invention may also be used as an accumulated exposure indicator, or dosimeter, in the same manner as was described for the previous embodiment of the invention. Also, while this invention has been explained as an x-ray to voltage transducer it should be appreciated that it may find use as a transducer with other types of radiation which causes the scintillating sheet to produce photons while the radiation passes therethrough to the solar cells which generate a voltage in response to both photons and radiation.

There has accordingly been described and shown hereinabove, a novel, useful and unique sensor for controlling the exposure to x-rays in order to obtain an optimum exposure result.

The embodiments of the invention in which an exclusive property or privilege is claimed are defined as follows:

1. In a system wherein an x-ray tube directs x-rays at one side of an object and a photographic film is positioned at the other side of said object, and means are provided for sensing the x-rays passing through said object and film for controlling the dose of x-ray exposure, the improvement in said means comprising
   scintillation means for generating photons in response to received x-rays which have passed through said film, and for enabling received x-rays to pass therethrough, said scintillation means being positioned to cover an area of said film where optimal exposure is desired,
   voltage generating means positioned adjacent to said scintillation means for generating a voltage responsive to the photons generated and x-rays passing therethrough,
   means for integrating the voltage generated by said voltage generating means to produce an integrated voltage, and
   means responsive to said integrated voltage reaching a predetermined value for inactivating said x-ray tube.

2. In a system as recited in claim 1 wherein said means responsive to said integrated voltage reaching a predetermined value, for inactivating said x-ray tube comprises
   a reference voltage source,
   means for comparing said integrated voltage with said reference voltage source and producing an output signal when they attain equality, and
   said means responsive to said integrated voltage reaching a predetermined value is rendered operative in response to said output signal.

3. In a system as recited in claim 1 wherein said voltage generating means comprises a plurality of solar cells connected in series.

4. In a system as recited in claim 1 wherein there is included
   means for indicating x-ray dosage responsive to the value of said integrated voltage.

5. In a system as recited in claim 1 wherein said scintillation means comprises a plurality of scintillation means spaced one behind another,
   said voltage generating means comprises a plurality of voltage generating means, each of which permits x-rays to pass therethrough, and each of which is positioned adjacent one of said scintillation means.

6. The method of controlling the level of exposure of a film to x-rays from an x-ray tube passing through a particular region of a subject to said film comprising
   generating photons in response to x-rays passing through said region and said film,
   generating a voltage in response to said photons and to said x-rays passing through said region and said film,
   integrating said voltage to produce an integrated voltage representative of the interval of exposure of said film, and
   inactivating said x-ray tube when said integrated voltage reaches a predetermined value representative of the desired exposure level.

7. The method as recited in claim 6 wherein said step of inactivating said x-ray tube when said integrated voltage reaches a predetermined value comprises
   establishing a reference voltage whose value is said predetermined value, and
   comparing said reference voltage with said integrated voltage and producing an output when they are equal,
   said step of inactivating occurs in response to said output.

8. An improved x-ray to voltage transducer comprising
   scintillation means for generating photons in response to received x-rays while enabling said received x-rays to pass therethrough, and
   means positioned adjacent to said scintillation means for generating a voltage in response to both x-rays passing through said scintillation means and said photons.

9. An improved x-ray to voltage transducer as recited in claim 8 wherein said means positioned adjacent to said scintillation means comprises
   solar cell means.

10. An improved x-ray to voltage transducer as recited in claim 9 wherein said solar cell means has an active area on the order of twenty square centimeters.

11. An improved x-ray to voltage transducer as recited in claim 9 including a container for holding said x-ray to voltage transducer, and
   handle means attached to said container for enabling the placement of said x-ray to voltage transducer at a desired location.

12. An improved x-ray to voltage transducer as recited in claim 8 wherein said scintillation means comprises
   a plurality of scintillation means spaced one behind another,
   said means positioned adjacent to said scintillation means for generating a voltage in response to both x-rays and photons comprises a plurality of said means for generating a voltage, each of which permits x-rays to pass therethrough, a different one of which is between said spaced scintillation means and a last one of which is adjacent the last of said scintillation means to receive x-rays and photons therefrom, and
   means for holding together said plurality of said scintillation means and said means for generating a voltage as successive layers.

13. An improved radiation to voltage transducer comprising
   a plurality of scintillation means for generating photons in response to received radiation while enabling said received radiation to pass therethrough, said plurality of scintillation means being spaced one behind the other,
   a plurality of means for generating a voltage in response to either or both x-rays and photons, each of which is positioned adjacent a different one of said plurality of scintillation means for generating a voltage in response to the photons produced by a scintillating means and the x-rays passing therethrough, and each of which can pass x-rays therethrough, and
   means for combining the voltage outputs of said plurality of means for generating a voltage, to produce a combined output.

14. An improved radiation to voltage transducer as recited in claim 13 wherein each of said plurality of means for generating a voltage comprises a plurality of solar cells, and
   means connecting each of said plurality of solar cells in series.

15. An improved radiation to voltage transducer as recited in claim 14 wherein said means for combining the voltage outputs of said plurality of means comprises means for adding all of said voltage outputs.

16. An improved radiation to voltage transducer as recited in claim 13 including
   means responsive to said combined voltage output for controlling the amount of radiation to which said transducer is exposed.

17. An improved radiation to voltage transducer as recited in claim 13 wherein there is included means responsive to said combined voltage outputs for indicating the amount of radiation received by a first of said spaced scintillation means.

18. In a system in which X-rays which are applied to one side of an object pass therethrough to be received by a film on the other side of the object, an improved radiation dosage indicator comprising:
   scintillation means for generating photons in response to received X-rays which have passed through said film, and for enabling received X-rays to pass therethrough, said scintillation means being positioned to cover an area of said film where optimal exposure is desired,
   voltage generating means positioned adjacent to said scintillation means for generating a voltage responsive to the photons generated and X-rays passing therethrough,
   means for integrating the voltage generated by said voltage generating means to produce an integrated voltage, and
   means responsive to said integrated voltage for indicating the amount of X-ray dosage received by said object.

* * * * *